(12) United States Patent
Kawahara

(10) Patent No.: US 7,692,797 B2
(45) Date of Patent: Apr. 6, 2010

(54) OPTICAL TOMOGRAPHY SYSTEM

(75) Inventor: Karin Kawahara, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 99 days.

(21) Appl. No.: 11/529,405

(22) Filed: Sep. 29, 2006

(65) Prior Publication Data
US 2007/0076220 A1 Apr. 5, 2007

(30) Foreign Application Priority Data
Sep. 30, 2005 (JP) ............................ 2005-289118
Mar. 16, 2006 (JP) ............................ 2006-072184

(51) Int. Cl.
G01B 11/02 (2006.01)
(52) U.S. Cl. ..................................... 356/497
(58) Field of Classification Search ................ 356/456, 356/479, 497, 506, 498, 499
See application file for complete search history.

(56) References Cited

U.S. PATENT DOCUMENTS

| 5,565,986 | A | | 10/1996 | Knüttel | |
|---|---|---|---|---|---|
| 6,101,034 | A | * | 8/2000 | Cox et al. | 359/562 |
| 6,377,349 | B1 | * | 4/2002 | Fercher | 356/497 |
| 6,847,454 | B2 | * | 1/2005 | Crowley et al. | 356/479 |
| 7,170,610 | B2 | * | 1/2007 | Knuttel | 356/456 |
| 7,355,716 | B2 | * | 4/2008 | de Boer et al. | 356/497 |
| 2004/0201850 | A1 | * | 10/2004 | Hajian et al. | 356/451 |
| 2004/0239938 | A1 | * | 12/2004 | Izatt | 356/450 |
| 2005/0018201 | A1 | * | 1/2005 | de Boer et al. | 356/479 |
| 2006/0039004 | A1 | * | 2/2006 | de Boer et al. | 356/479 |
| 2006/0066869 | A1 | * | 3/2006 | Ueno et al. | 356/497 |
| 2006/0119858 | A1 | * | 6/2006 | Knighton et al. | 356/479 |
| 2007/0024856 | A1 | * | 2/2007 | Izatt et al. | 356/456 |
| 2007/0081166 | A1 | * | 4/2007 | Brown et al. | 356/479 |
| 2007/0133002 | A1 | * | 6/2007 | Wax et al. | 356/456 |

FOREIGN PATENT DOCUMENTS

JP 11-82817 A 3/1999
JP 2003-172690 A 6/2003

* cited by examiner

Primary Examiner—Gregory J Toatley, Jr.
Assistant Examiner—Scott M Richey
(74) Attorney, Agent, or Firm—Sughrue Mion, PLLC

(57) ABSTRACT

An optical tomography system for obtaining a tomographic image of an object to be measured includes a light source unit which emits low coherence light. The low coherence light emitted from the light source unit is divided into measuring light and reference light. The reflected light from the object when the measuring light is projected onto the object and the reference light are multiplexed. The interference light of the reflected light and the reference light which have been multiplexed is detected, and a tomographic image information of the object is obtained by carrying out frequency-analysis on the detected interference light. A first detecting mode in which the interference light is detected at a first wavelength resolution and the interference light is detected at a second wavelength resolution higher than the first wavelength resolution are switched.

12 Claims, 12 Drawing Sheets $$\Gamma = \frac{\lambda_0^2}{\Delta l}$$

OPTICAL TOMOGRAPHY SYSTEM

BACKGROUND OF THE INVENTION

1. Field of the Invention

This invention relates to an optical tomography system for obtaining an optical tomographic image by measurement of OCT (optical coherence tomography).

2. Description of the Related Art

As a system for obtaining a tomographic image of an object of measurement in a body cavity, there has been known an ultrasonic tomography system. In addition to such an ultrasonic tomography system, there has been proposed an optical tomography system where an optical tomographic image is obtained on the basis of an interference of light by low coherence light. See, for instance, Japanese Unexamined Patent Publication No. 2003-172690. In the system disclosed in Japanese Unexamined Patent Publication No. 2003-172690, an optical tomographic image is obtained by measuring TD-OCT (time domain OCT) and the measuring light is guided into the body cavity by inserting a probe into the body cavity from the forceps port of an endoscope by way of a forceps channel.

More specifically, low coherence light emitted from a light source is divided into measuring light and reference light and the measuring light is projected onto the object of measurement, while the reflected light from the object of measurement is led to a combining means. The reference light is led to the combining means after its optical path length is changed. By the combining means, the reflected light and the reference light are superposed one on another, and interference light due to the superposition is detected by, for instance, heterodyne detection. In the TD-OCT measurement, a phenomenon that interference light is detected when the optical path of the measuring light conforms to the optical path of the reference light in length is used and the measuring position (the depth of measurement) in the object is changed by changing the optical path length of the reference light.

When measuring the OCT by inserting a probe into a body cavity, the probe is mounted on the system body to be demountable since disinfection, cleaning and the like of the probe after use are necessary. That is, a plurality of probes are prepared for one optical tomography system and the probes are changed by the measurement. However there is an individual difference in the length of the optical fiber due to the manufacturing errors and the like, and the optical path length of the measuring light can change each time the probe is changed. Accordingly, in Japanese Unexamined Patent Publication No. 2003-172690, on the basis of the reflected light from the inner surface of a tube (sheath) covering an optical fiber of the probe, the optical path length of the reference light is adjusted to conform to the optical path length of the measuring light.

Whereas, as a system for rapidly obtaining a tomographic image without sweeping the optical path length of the reference light such as disclosed in Japanese Unexamined Patent Publication No. 2003-172690, there have been proposed optical tomography systems of obtaining an optical tomographic image by spatially or time dividing the interference light (See, for instance, U.S. Pat. No. 5,565,986 or Japanese Unexamined Patent Publication No. 11(1999)-82817). Among those, a SD-OCT (source domain OCT) system where the frequency of light emitted from a light source is spatially divided to detect the interference light altogether has been proposed. In the SD-OCT system, a tomographic image is formed without scanning in the direction of depth, by emitting broad band, low coherence light from a light source by the use of a Michelson interferometer, dividing the low coherence light into measuring light and reference light and carrying out a Fourier analysis on each channeled spectrum obtained by decomposing the interference light of the reflected light, which returns when projecting the measuring light onto the object, and the reference light into frequency components.

SUMMARY OF THE INVENTION

In the SD-OCT measurement, it is not necessary to conform the optical path length of the measuring light to that of the reference light since information on the reflection in positions in the direction of depth can be obtained by carrying out frequency-analysis. However, there arises a problem that when the optical path length difference becomes large, the spatial frequency of the interference signal is enlarged and the S/N of the detected interference signal deteriorates due to limitation by the number of arrays in the array detector for detecting the interference light. Accordingly, also in the SD-OCT measurement, it is still necessary to adjust the optical path length so that the optical path length of the measuring light conforms to that of the reference light and the measurement initiating position is adjusted to a position in which the object is included in the measurable range.

The measurable range (measuring depth) over which a tomographic image is obtainable by the SD-OCT measurement is reverse proportional to the wavelength band of the low coherence light (the wavelength band of the interference light), and the resolution when a tomographic image is obtained increases as the wavelength band of the low coherence light becomes wider. That is, the measurable range becomes narrow when a tomographic image is obtained at a high resolution with the detector of the same number of arrays. Accordingly, it takes a long time to bring the optical path length difference between the measuring light and the reference light to the measurable range since the measurable range (measuring depth) is narrow to obtain a tomographic image in order to adjust the measurement initiating position in an SD-OCT system for obtaining a high resolution tomographic image. Similarly, for instance, when the layer arrangement of the stomach wall is to be observed, a tomographic image cannot be obtained at a desired measurable range (measuring depth).

In view of the foregoing observations and description, the primary object of the present invention is to provide an optical tomography system which is improved in convenience and can switch the measurable range (measuring depth) according to the application in an optical tomography system where optical cross-sectional image is obtained by projecting low coherence light which is broad in wavelength band onto the object and carrying out frequency-analysis on the interference light at that time.

In accordance with the present invention, there is provided an optical tomography system for obtaining a tomographic image of an object to be measured comprising a light source unit which emits low coherence light, a light dividing means which divides the low coherence light emitted from the light source unit into measuring light and reference light, a combining means which combines the reflected light, which is reflected from the object when the measuring light is projected onto the object, and the reference light, an interference light detecting means which detects interference light of the reflected light and the reference light which have been combined by the combining means, and a tomographic image information obtaining means which obtains a tomographic image information of the object by carrying out frequency-analysis on the interference light detected by the interference light detecting means, wherein the improvement comprises that the interference light detecting means can be switched between a first detecting mode in which the interference light detecting means detects the interference light at a first wavelength resolution and a second detecting mode in which the interference light detecting means detects the interference light at a second wavelength resolution higher than the first wavelength resolution.

The interference light detecting means may be of any arrangement.

The interference light detecting means may comprise a spectral means which spectrally divides the interference light, an optical sensor which detects the interference light divided by the spectral means and comprises a plurality of arranged photo-sensors, and a wavelength bandwidth switching means which switches the wavelength bandwidth of the interference light entering the optical sensor. This wavelength bandwidth switching means switches the wavelength bandwidth so that the wavelength bandwidth of the interference light entering the optical sensor in the second detecting mode is narrower than the wavelength bandwidth of the interference light entering the optical sensor in the first detecting mode. It is preferred that the wavelength bandwidth of the interference light entering the optical sensor in the second detecting mode be a part of the wavelength bandwidth of the interference light entering the optical sensor in the first detecting mode. The wavelength bandwidth switching means may be any so long as it can switch the wavelength bandwidth of the interference light entering the optical sensor. For example, the wavelength bandwidth switching means may switch the wavelength bandwidth of the interference light entering the optical sensor by switching the distance between the spectral means and the optical sensor.

Otherwise, the wavelength bandwidth switching means may comprise a magnification switching means which switches the magnification of the interference light entering the optical sensor. The magnification switching means may be any so long as it can switch the magnification by the interference light, and, for instance, may be those where a magnifier lens is inserted between the optical sensor and the spectral means or those where a collective lens which has been disposed is changed for a collective lens different in magnification.

The magnification switching means may further be a zoom lens which is disposed between the optical sensor and the spectral means to collect the interference light divided by the spectral means on the optical sensor at various magnifications.

The zoom lens may be either a lens where its magnification stepwise varies or a lens where its magnification continuously varies.

Further, the wavelength bandwidth switching means may comprise a spectral angular width changing means which switches the spectral angular width of the interference light. "Spectral angular width" means the difference between the spectral angle of the minimum wavelength of the interference light and the spectral angle of the maximum wavelength of the interference light when the interference light of a predetermined wavelength bandwidth is spectrally divided. The wavelength bandwidth switching means switches the spectral angular width so that the spectral angular width is larger in the second detecting mode than in the first detecting mode.

Further, the wavelength bandwidth switching means may comprise a plurality of diffraction gratings different in grating spaces and a diffraction grating selecting means which selectively disposes in a spectral dividing position where the interference light can be spectrally divided by one of the diffraction gratings. In the first detecting mode, the diffraction grating which is large in the grating space where the spectral angular width is narrowed is selected while in the second detecting mode, the diffraction grating which is small in the grating space where the spectral angular width is wide is selected.

Further, the interference light detecting means may comprise a spectral means which spectrally divides the interference light, an optical sensor which detects the interference light divided by the spectral means and comprises a plurality of arranged photo-sensors, and a wavelength switching means which switches the wavelength of the interference light received by the photo-sensors so that the photo-sensors detect light of different wavelengths at different times. That "the photo-sensors detect light of different wavelengths at different times" means that a photo-sensor does not detect light of a wavelength which has been previously detected by the photo-sensor or another photo-sensor.

The wavelength switching means may comprise a slit element having a slit narrower than a light receiving face of each of the photo-sensors in a width in a direction in which the photo-sensors are arranged and a slit moving means which moves the slit element in the direction in which the photo-sensors are arranged. The slit element only has to have one or more slits. For example, when the number of slits are the same as the number of the photo-sensors, it is preferred that the slits be disposed so that the interference light passing through the slits is spaced from each other on the optical sensor at the same spaces as the photo-sensors. In this case, the photo-sensors, for instance, may be moved by 0.5 or 1.5 pieces of photo-sensors so that the wavelength does not move at the same spaces as the photo-sensors.

Further, the wavelength switching means may comprise an optical sensor moving means which moves the optical sensor so that the wavelength bandwidth of the interference light entering the photo-sensors is changed. However, the cases where the movement of the optical sensor is an integer times as large as the space between the photo-sensors are not included so that the photo-sensors detect light of different frequencies at different times.

The wavelength switching means may comprise an optical path shift means which spatially shifts the optical path of the interference light so that the wavelength bandwidth of the interference light entering the photo-sensors is different at different times. The optical path shift means may be any so long as it spatially shifts the optical path of the interference light.

The optical path shift means may comprise a spectral means moving means which moves the spectral means so that the wavelength band of the interference light entering the photo-sensors is different at different times. The spectral means moving means may rotate the spectral means or may translate the spectral means so that the spectrally dividing position changes. Further, the optical path shift means may comprise a collective lens which is disposed between the optical sensor and the spectral means and collects the interference light which has been spectrally divided by the spectral means on the optical sensor and a collective lens moving means which moves the collective lens so that the wavelength band of the interference light entering the photo-sensors is different at different times. The collective lens moving means may be either a means for moving the collective lens in the direction in which the photo-sensors are arranged or a means for inclining the collective lens.

When the first detecting mode is an image obtaining mode where a tomographic image of the object is obtained and the second detecting mode is a measurement initiating position adjusting mode where a position of obtaining a tomographic image signal is adjusted in the direction of depth of the object, the optical tomography system may further comprise a control means which switches between the image obtaining mode and the measurement initiating position adjusting mode.

The optical tomography system may further comprise an optical path length adjusting means which adjusts the optical path length of the measuring light or the reference light.

A wavelength forming filter may be inserted in the optical path of the low coherence light or the measuring light.

Further, so long as the optical tomography system comprises a means for measuring the spectral components of the measuring light and a memory means for storing the measured spectral components, the tomographic image information obtaining means may obtain the tomographic image information of the object on the basis of a compensating signal by generating the compensating signal by removing the spectral components of the measuring light stored in the memory means from an interference signal detected by the interference light.

The interference light detecting means may comprise a spectral means which spectrally divides the interference light, an optical sensor which comprises a plurality of arranged photo-sensors which detect the spectrally divided interference light, a wavelength bandwidth switching means which switches the wavelength bandwidth of the interference light entering the optical sensor, and a wavelength switching means which switches the wavelength of the interference light received by the photo-sensors so that the photo-sensors detect light of different frequencies at different times.

Since, in the optical tomography system of the present invention comprising a light source unit which emits low coherence light, a light dividing means which divides the low coherence light emitted from the light source unit into measuring light and reference light, a combining means which combines the reflected light from the object when the measuring light divided by the light dividing means is projected onto the object and the reference light, an interference light detecting means which detects interference light of the reflected light and the reference light which have been combined by the combining means, and a tomographic image information obtaining means which obtains a tomographic image information of the object by carrying out frequency-analysis on the interference light detected by the interference light detecting means, the measurable range (measuring depth) increases as the wavelength resolution increases and decreases as the wavelength resolution decreases, the user can switch the measurable range (measuring depth) according to the application, whereby the convenience of the optical tomography system is improved, when the interference light detecting means can be switched between a first detecting mode in which the interference light detecting means detects the interference light at a first wavelength resolution and a second detecting mode in which the interference light detecting means detects the interference light at a second wavelength resolution higher than the first wavelength resolution.

When the interference light detecting means comprises a spectral means which spectrally divides the interference light, an optical sensor which detects the interference light divided by the spectral means and comprises a plurality of arranged photo-sensors, and a wavelength bandwidth switching means which switches the wavelength bandwidth of the interference light entering the optical sensor, the user can easily obtain an optical tomographic image which is larger in the measurable range (measuring depth) and the convenience of the optical tomography system is improved by switching the wavelength bandwidth so that the wavelength bandwidth of the interference light entering the optical sensor in the second detecting mode is narrower than the wavelength bandwidth of the interference light entering the optical sensor in the first detecting mode.

Further, when the interference light detecting means comprises a spectral means which spectrally divides the interference light, an optical sensor which comprises a plurality of arranged photo-sensors which detect the spectrally divided interference light, and a wavelength switching means which switches the wavelength of the interference light received by the photo-sensors so that the photo-sensors detect light of different frequencies at different times, an optical tomographic image which is larger in the measurable range (measuring depth) can be obtained without deteriorating the measuring resolution since the wavelength bandwidth of the interference light entering the optical sensor is kept unchanged and the convenience of the optical tomography system is further improved.

Further, when the interference light detecting means comprises a spectral means which spectrally divides the interference light, an optical sensor which comprises a plurality of arranged photo-sensors which detect the spectrally divided interference light, a wavelength bandwidth switching means which switches the wavelength bandwidth of the interference light entering the optical sensor, and a wavelength switching means which switches the wavelength of the interference light received by the photo-sensors so that the photo-sensors detect light of different frequencies at different times, the wavelength bandwidth switching means and the wavelength switching means can be selectively used according to the application. For instance, when a large measuring resolution is not needed as when a position in which a tomographic image signal is to be obtained is adjusted in the direction of depth of the object, the wavelength bandwidth is switched by the wavelength bandwidth switching means to enlarge the wavelength resolution in the interference light detecting means, whereby an optical tomographic image which is larger in the measurable range (measuring depth) can be obtained without increasing the measuring time. Further, when a large measuring resolution is needed as when the layer arrangement of the stomach wall is to be observed, the wavelength of the interference light received by the photo-sensors is switched by the wavelength switching means so that the photo-sensors detect light of different frequencies at different times to enlarge the wavelength resolution in the interference light detecting means, whereby an optical tomographic image which is larger in the measurable range (measuring depth) can be obtained without deteriorating the measuring resolution though the measuring time is increased.

DESCRIPTION OF THE PREFERRED EMBODIMENTS

Figure 1:
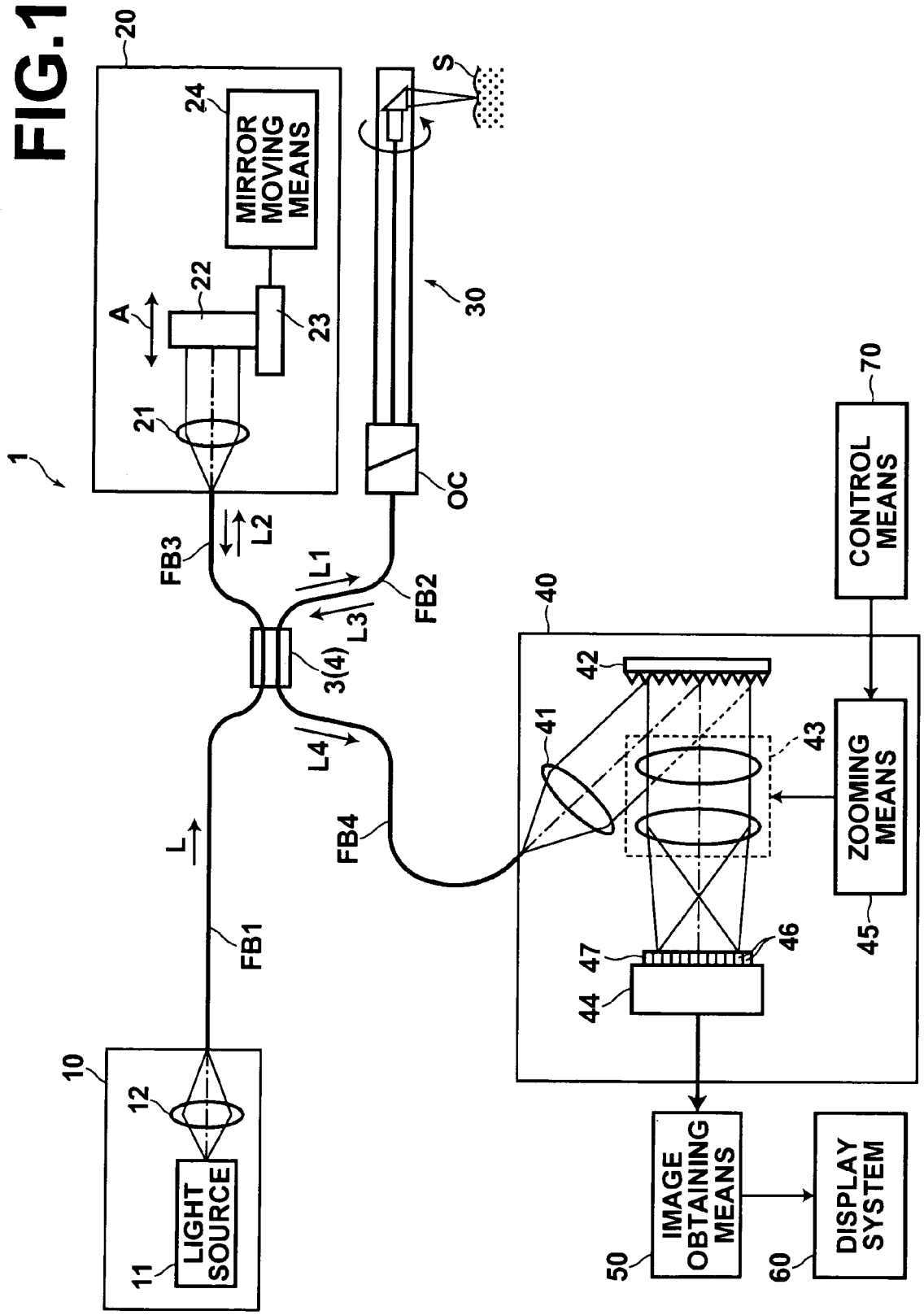
FIG. 1 is a schematic diagram showing an optical tomography system in accordance with a preferred embodiment of the present invention.

Embodiments of the optical tomography system of the present invention will be described in detail with reference to the drawings, hereinbelow. FIG. 1 is a schematic diagram that illustrates an optical tomography system in accordance with a preferred embodiment of the present invention. The optical tomography system 1 of this embodiment is for obtaining a tomographic image of an object of measurement such as a living tissue or a cell in a body cavity by measuring the SD-OCT. The optical tomography apparatus 1 of this embodiment comprises: a light source unit 10 for emitting a low coherence light beam L; a light dividing means 3 for dividing the light beam L emitted from the light source unit 10 into a measuring light beam L1 and a reference light beam L2; an optical path length adjusting means 20 for adjusting the optical path length of the reference light beam L2 divided by the light dividing means 3; a probe 30 which guides to the object S to be measured the measuring light beam L1 divided by the light dividing means 3; a combining means 4 for combining a reflected light beam L3 from the object S when the measuring light beam L1 is irradiated onto the object S from the probe 30, and the reference light beam L2; an interference light detecting means 40 for detecting interference light beam L4 of the reflected light beam L3 and the reference light beam L2 which have been combined and an image obtaining means 50 which obtains a tomographic image of the object S by carrying out frequency-analysis on the interference light beam L4 detected by the interference light detecting means 40.

Figure 2:
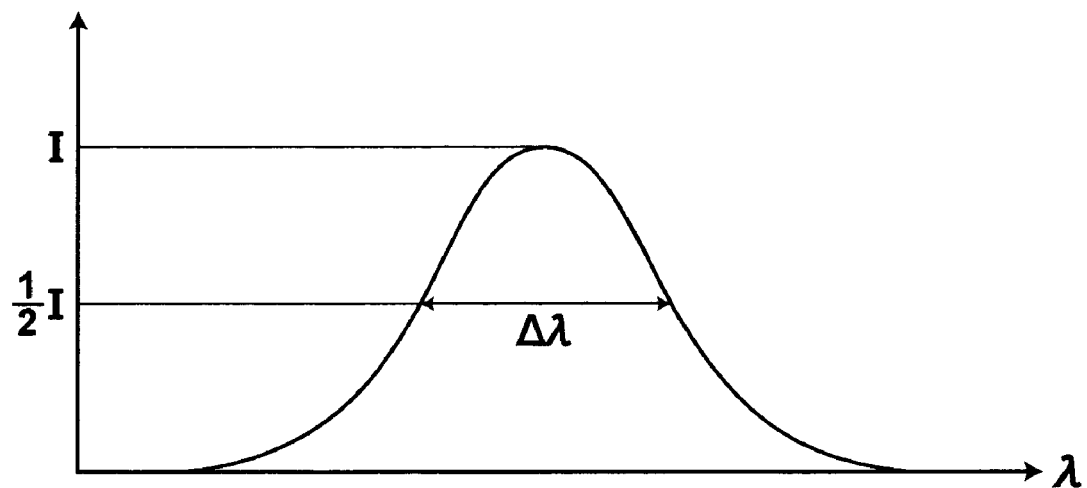
FIG. 2 is a view for illustrating an example of the low coherence light output from the light source unit shown in FIG. 1, FIGS. 3A to 3C are views for illustrating an example of the interference light detected in the interference light detecting means shown in FIG. 1.

The light source unit 10 comprises a light source 11 which emits low coherence light such as SLD (super luminescent diode) or ASE (amplified spontaneous emission) and an optical system 12 for entering the light emitted from the light source 111 into an optical fiber FB1. From the light source unit 10, low coherence light L having a wavelength band and a half bandwidth $\Delta\lambda$ such as shown in FIG. 2 is emitted.

The light dividing means 3 shown in FIG. 1 comprises, for instance, a 2×2 fiber optic coupler and divides the light beam L led thereto by way of the optical fiber FB1 from the light source unit 10 into the measuring light beam L1 and the reference light beam L2. The light dividing means 3 is optically connected to two optical fibers FB2 and FB3, and the measuring light beam L1 is propagated through the optical fiber FB2 while the reference light beam L2 is propagated through the optical fiber FB3. In FIG. 1, the light dividing means 3 also functions as the combining means 4.

The probe 30 is optically connected to the optical fiber FB2 and the measuring light beam L1 is guided to the probe 30 from the optical fiber FB2. The probe 30 is inserted into a body cavity, for instance, through a forceps port by way of a forceps channel and is removably mounted on the optical fiber FB2 by an optical connector OC.

The optical path length adjusting means 20 is disposed on the side of the optical fiber FB3 radiating the reference light beam L2. The optical path length adjusting means 20 changes the optical path length of the reference light beam L2 in order to adjust the measurement initiation position with respect to the object S and comprises a collimator lens 21 and a reflecting mirror 22. The reference light beam L2 radiated from the optical fiber FB3 is reflected by the reflecting mirror 22 after passing through the collimator lens 21 and reenters the optical fiber FB3 again through the collimator lens 21.

The reflecting mirror 22 is disposed on a movable stage 23 which is moved in the direction of arrow A by a mirror moving means 24. In response to movement of the movable stage 23 in the direction of arrow A, the optical path length of the reference light L2 is changed.

The combining means 4 comprises a 2×2 fiber optic coupler, and combines the reference light beam L2 which has been changed in its optical path length and shifted in its frequency by the optical path length adjusting means 20 and the reflected light beam L3 from the object S to emit the combined light beam toward an interference light detecting means 40 by way of an optical fiber FB4.

The interference light detecting means 40 detects interference light L4 of the reflected light beam L3 and the reference light beam L2 which have been combined by the combining means 4 and comprises a spectral means 42 which spectrally divides the interference light L4 having a predetermined wavelength band by the wavelength band, a light detecting means 44 which detects the amount light by the wavelengths of the interference light L4 divided by the spectral means 42, a zoom lens 43 which is disposed between the optical sensor 44 and the spectral means 42 and has a function of imaging the interference light L4 spectrally divided by the spectral means 42 on the light detecting means 44, and a zooming means 45 which drives the zoom lens 43 so that the wavelength bandwidth of the interference light L4 imaged on the light detecting means 44 by the zoom lens 43 is changed.

The spectral means 42 comprises, for instance, a diffraction grating element, and divides the interference light beam L4 entering it from an optical fiber FB4 by way of a collimator lens 41 to emit the divided interference light beam L4 to the light detecting means 44. The zoom lens 43 collects the divided interference light beam L4 on the light detecting means 44. In response to drive by the zooming means 45, the zoom lens 43 changes the size of the image of the interference light L4 formed on the light detecting means 44. The light detecting means 44 comprises an optical sensor 47 which comprises a plurality of one-dimensionally arranged photosensors 46 such as CCDs or photodiodes and the photosensors 46 detect the interference light L4 impinging thereupon by way of the zoom lens 43 by the wavelength band. The optical sensor 47 may comprise a plurality of two-dimensionally arranged photo-sensors 46. In this case, when the photo-sensors are arranged perpendicularly to the plane of paper of FIG. 1, for instance, the average of the detecting values of the photo-sensors or the sum of the detecting values of the photo-sensors may be used as the detecting value of the optical sensor 47.

The image obtaining means 50 may obtain information on reflection of the positions in the direction of depth of the object S by carrying out frequency analysis on the interference light beam L4 detected by the interference light detecting means 40. The image obtaining means 50 obtains an image of the object S by using the intensities of the reflected light beam L3 in positions in the direction of depth of the object S. Then the tomographic image is displayed in a display 60.

Here, detection of the interference light beam L4 in the interference light detecting means 40 and image generation in the image obtaining means 50 will be described briefly. Note that a detailed description of these two points can be found in M. Takeda, "Optical Frequency Scanning Interference Microscopes", Optical Engineering Contact, Vol. 41, No. 7, pp. 426-432, 2003.

When the measuring light beam L1 having a spectral intensity distribution of S(k), the light intensity I(k) detected in the interference light detecting means 40 as the interferogram is expressed by the following formula.

$$I(l) = \int_0^\infty S(k)[1+\cos(kl)]dk \quad (1)$$

wherein k represents the angular frequency and l represents the optical path length difference between the measuring light beam L1 and the reference light beam L2. Formula (1) expresses how much components of the angular frequency k of the interference fringe I(l) are included in the interference fringe I(l) where the spectral intensity distribution of each spectral component is S(k). Further, from the angular frequency k of the interference light fringes, the optical path length difference between the measuring light beam L1 and the reference light beam L2, that is, information on the position of depth, is given. Accordingly, S(k) of the interference light L4 can be obtained by carrying out frequency analysis by Fourier-transform on the interferogram detected by the interference light detecting means 40 in the image obtaining means 50. Then a tomographic image is generated by obtaining information on the distance of the object S from the measurement initiating position and information on the intensity of reflection. The generated tomographic image is displayed in the display 60.

Operation of the optical tomography system 1 will be described with reference to FIGS. 1 and 2, hereinbelow. When a tomographic image is to be obtained, the optical path length is first adjusted by moving the movable stage 23 in the direction of the arrow A so that the object S is positioned in the measurable area. The low coherence light beam L is subsequently emitted from the light source unit 10 and the low coherence light beam L is divided into the measuring light beam L1 and the reference light beam L2 by the light dividing means 3. The measuring light beam L1 is led by the optical probe 30 into a body cavity and is projected onto the object S. Then the reflected light beam L3 from the object S and the reference light beam L2 reflected by the reflecting mirror 22 are combined, and the interference light beam L4 of the reflected light beam L3 and the reference light beam L2 is detected by the interference light detecting means 40. A tomographic image is obtained by carrying out frequency analysis on a signal of the detected interference light beam L4 in the image obtaining means 50. In the optical tomography system 1 where a tomographic image is obtained by the SD-OCT measurement, the image information in positions in the direction of depth is obtained on the basis of the frequency and the intensity of the interference light L4 and the movement of the reflecting mirror 22 in the direction of arrow A is used for adjustment of the position in which a tomographic image is to be obtained in the direction of depth of the object S.

In the SD-OCT measurement described above, when the optical path length difference between the measuring light beam L1 and the reference light beam L2 becomes large, the number of photo-sensors in the optical sensor 47 is limited and quality of the image deteriorates due to increase in the spatial frequency and/or the like. Accordingly, it is necessary to adjust the optical path length so that the optical path lengths of the measuring light beam and the reference light beam conform to each other. The measurable range (measuring depth) is reverse proportional to the wavelength band width of the interference light L4 entering the optical sensor 47, and the resolution when a tomographic image is obtained increases as the wavelength band width becomes wider. That is, the measurable range becomes narrow when a tomographic image is obtained at a high resolution with the detector of the same number of arrays. Accordingly, it takes a long time to bring the optical path length difference between the measuring light and the reference light to the measurable range since the measurable range (measuring depth) is narrow to obtain a tomographic image in order to adjust the measurement initiating position in an SD-OCT system for obtaining a high resolution tomographic image.

Accordingly, the optical tomography system 1 shown in FIG. 1 is provided with a control means 70 which switches between a measurement initiating position adjusting mode where a position for obtaining a tomographic image signal is adjusted in the direction of depth of the object S and an image obtaining mode where a tomographic image of the object S is obtained. The control means 70 controls the interference light detecting means 40 so that the wavelength resolution of the interference light detecting means 40 is higher in the measurement initiating position adjusting mode than in the image obtaining mode.

As two methods of improving the wavelength resolution of the interference light detecting means 40 in the measurement initiating position adjusting mode, there is a method in which the wavelength band width is switched so that the wavelength band width of the interference light beam L4 entering the optical sensor 47 in the measurement initiating position adjusting mode is narrower than that of the interference light beam L4 entering the optical sensor 47 in the image obtaining mode and a method in which the wavelength of the interference light beam L4 received by the photo-sensors 46 is switched so that the photo-sensors 46 detect the interference light beam L4 of different frequencies at different times.

Figure 3C:
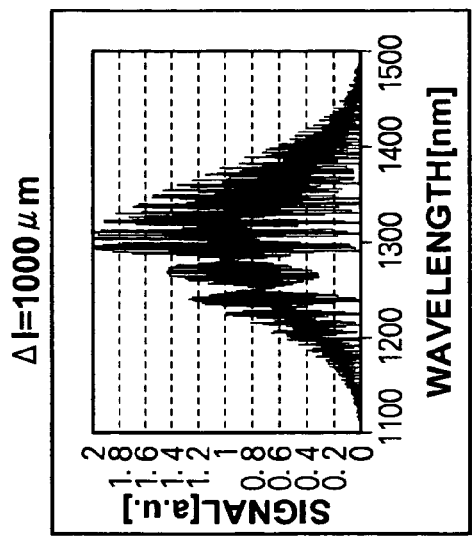
Figure 3B:
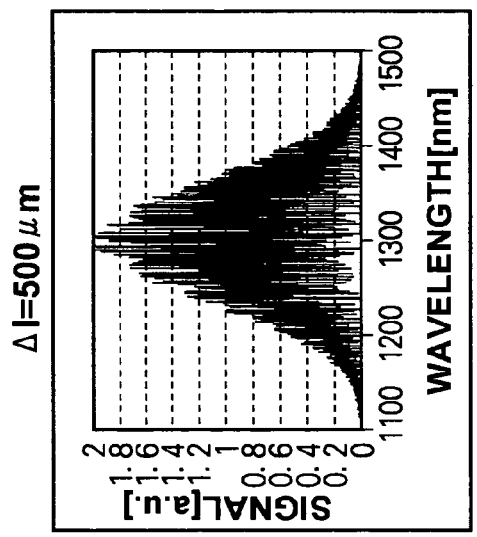
Figure 3A:
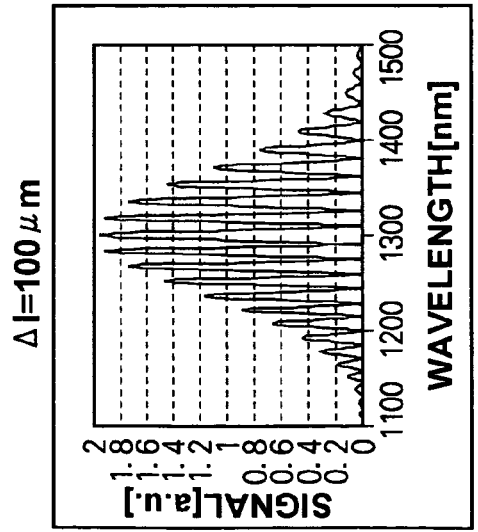
Figure 4:
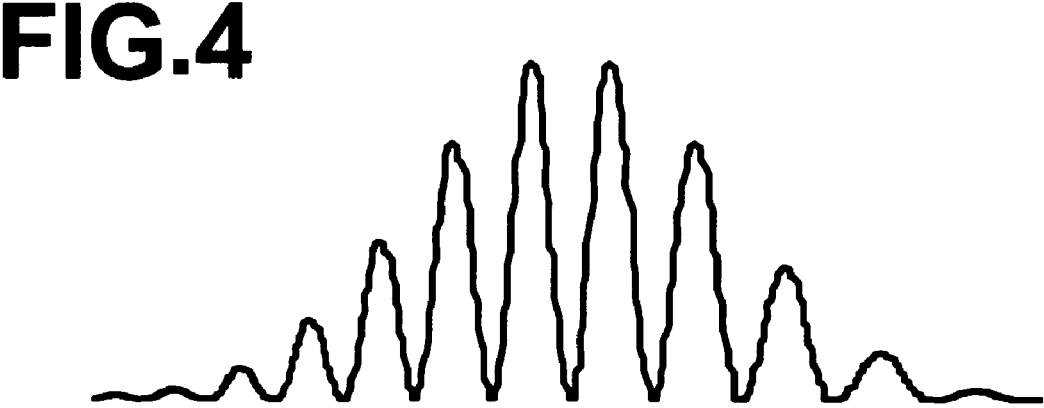
FIG. 4 is a view for illustrating an example of the interference light detected in the interference light detecting means shown in FIG. 1, FIGS. 5A and 5B are schematic diagrams showing a preferred example of the interference light detected in the interference light detecting means shown in FIG. 1, FIGS. 6A and 6B are schematic diagrams showing a second example of the interference light detected in the interference light detecting means in the optical tomography system of the present invention.

That is, assuming that the optical path length difference $\Delta l$ between the optical path length ls of the measuring light beam L1 and the optical path length lr of the reference light beam L2 is $\Delta l=|lr-ls|$, the period $\Gamma$ of the interference light beam L4 detected by the interference light detecting means 40 such as shown in FIG. 4 is expressed by the following formula.

$$\Gamma = \lambda o^2/\Delta l \quad (2)$$

wherein $\lambda o$ represents the central wavelength of the interference light beam L4. FIGS. 3A, 3B and 3C respectively show the waveforms of the interference light beam L4 detected by the interference light detecting means 40 whose number of photo-sensors are 512 (N=512), when $\Delta l=100$ μm, $\Delta l=500$ μm, $\Delta l=1000$ μm. As can be understood from FIGS. 3A, 3B and 3C, as the optical path length difference $\Delta l$ increases, the period $\Gamma$ of the interference light beam L4 becomes shorter.

In order to obtain a signal at a sufficient resolution, four or more than four sampling per one period of fluctuation of the low coherence light L is necessary as follows.

$$\text{wavelength resolution=sampling periods} \Delta\xi < \text{period of the interference light beam} \Gamma/4 \quad (3)$$

When formula (3) is not satisfied, the period $\Gamma$ of the interference light beam L4 exceeds the wavelength resolution of the interference light detecting means 40 as shown in FIGS. 3C and S/N deteriorates, which results in deterioration of the quality of the image. Further, the wavelength resolution is governed by the wavelength band $\Delta\Lambda$ of the interference light beam L4 entering the optical sensor 47 and the number N of the photo-sensors 46 forming the optical sensor 47 and equal to the sampling periods $\Delta\xi=\Delta\Lambda/N$. Accordingly, the final measurable depth $\Delta l lim$ of the object S is as follows from the formulae (2) and (3).

$$\Delta l lim = \frac{1}{4} \cdot \lambda o^2 N/\Delta\Lambda \quad (4)$$

Formula (4) represents that the tomographic image obtainable range is reverse proportional to the wavelength band $\Delta\Lambda$ of the interference light L4 entering the optical sensor 47 and proportional to the number N of the photo-sensors.

Accordingly, the spectrum of the interference light beam 4 is partly detected and the wavelength band $\Delta\Lambda$ of the interference light beam L4 entering the optical sensor 47 is narrowed. Then the wavelength resolution is improved and the measurable depth $\Delta l lim$ is enlarged as shown in formula (4). As specific methods, for instance, a method where a zoom lens is employed as shown in FIGS. 5A and 5B and a method where a spectral means is employed as shown in FIGS. 6A and 6B are conceivable.

Figure 5A:
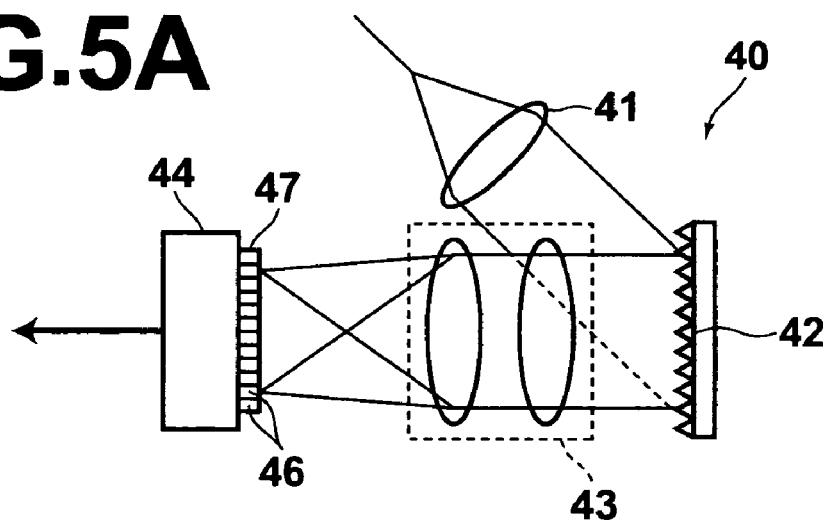
Figure 5B:
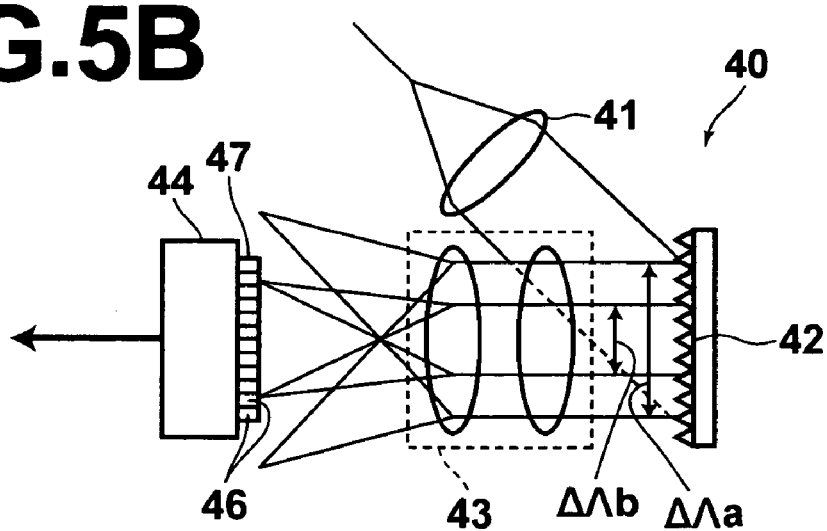

In FIG. 5A, in the image obtaining mode, the control means 70 controls the zooming means 45 so that almost the whole wavelength band $\Delta\Lambda$ of the interference light beam L4 enters the optical sensor 47 by the zoom lens 43. Whereas, in the measurement initiating position adjusting mode, the control means 70 controls the zooming means 45 as shown in FIG. 5B so that wavelength band $\Delta\Lambda$ of the interference light beam L4 partly enters the optical sensor 47 by the zoom lens 43. With this arrangement, the wavelength band to be detected by each of the photo-sensors 46 of the optical sensor 47 is narrowed and the wavelength resolution of the light detecting means 44 is improved. Accordingly, the measurable range $\Delta l lim$ can be enlarged.

Figure 6A:
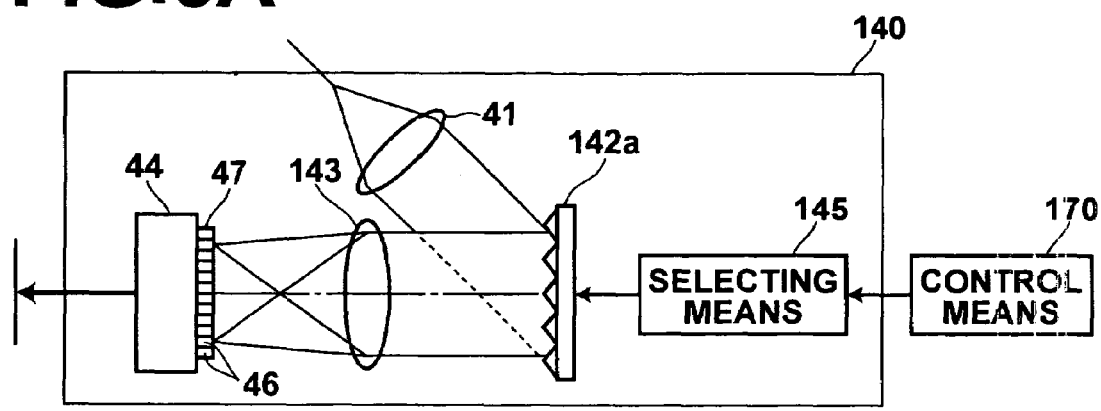
Figure 6B:
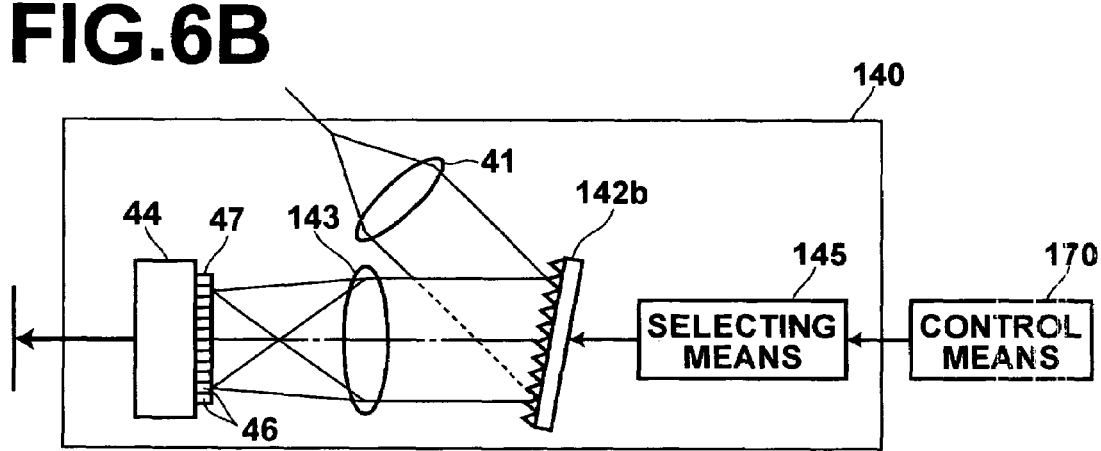
Figure 17:
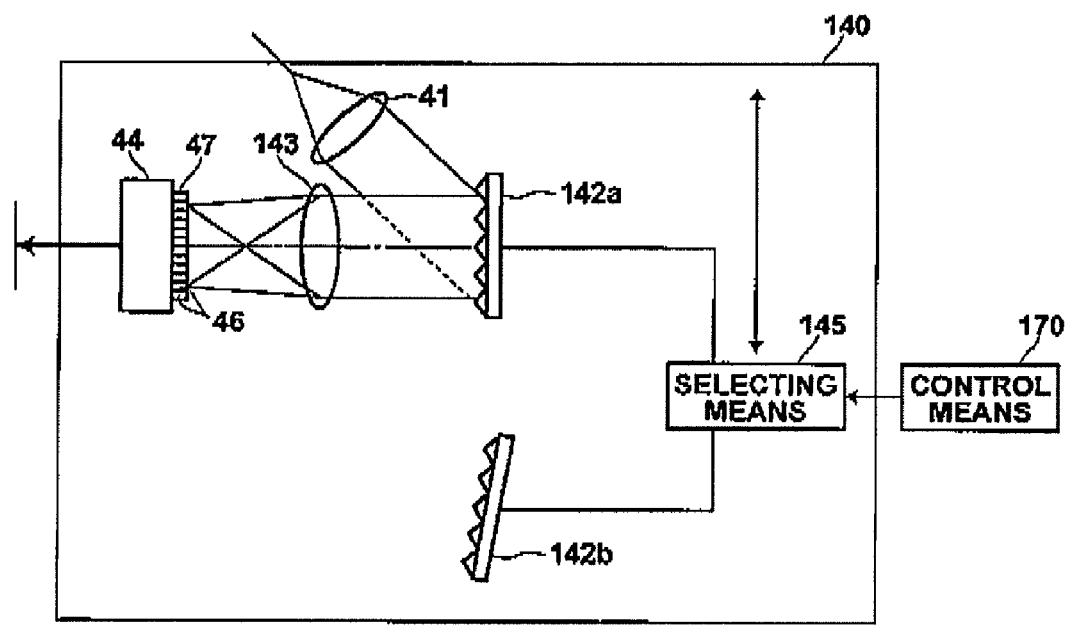
FIG. 17 is a schematic diagram showing the second example of the interference light detected in the interference light detecting means in the optical tomography system of the present invention.

On the other hand, the spectral means 140 shown in FIGS. 6A and 6B has a pair of diffraction grating elements 142a and 142b. Which of the two diffraction grating elements 142a and 142b is to be employed is selected by a selecting means 145, which is controlled by the control means 170. For example, FIG. 17 illustrates the spectral means 140 having the pair of diffraction grating elements 142a and 142b. The diffraction grating elements 142a and 142b are alternatively selected by the selecting means 145, which is controlled by the control means 170. For example, the diffraction grating elements 142a and 142b are selected by moving the selected diffraction grating (142a or 142b) by the selecting means 145 into a position to spectrally divide the interference light beam L4. A lens 143 for imaging the spectrally divided interference light beam L4 on the light detecting means 44 is disposed between the diffraction grating element 142a (142b) and the light detecting means 44.

The control means 170 controls the selecting means 145 to select a wider (wider in intervals between gratings) diffraction grating element 142a in the image obtaining mode so that a wavelength band of interference light beam L4 sufficient to obtain a desired resolution out of the divided light is collected on the light detecting means 44 as shown in FIG. 6A. Whereas, the control means 170 controls the selecting means 145 to select a narrower (narrower in intervals between gratings) diffraction grating element 142b in the measurement initiating position adjusting mode so that a wavelength band of interference light beam L4 narrower than that collected on the light detecting means 44 in the image obtaining mode is collected on the light detecting means 44 as shown in FIG. 6B.

For example, it is assumed that the wavelength band of $\Delta\Lambda=200$ nm is measured with low coherence light beam which is 1.3 μm in the central wavelength ($\lambda 0=1.3$ μm) and 150 nm in $\Delta\lambda$ ($\Delta\lambda=150$ nm) and that the diffraction gratings 142a and 142b are 600 line/mm and 1200 line/mm in intervals between gratings (Ng1=600 line/mm, Ng2=1200 line/mm).

In this case, when the diffraction grating 142a is employed in the image obtaining mode as shown in FIG. 6A, the radiation angle $\beta$ when the interference light beam L4 impinges upon the spectral means 43 form the optical fiber FB4 at angle of incidence $\alpha=45°$ is $-3°$ (1.1 μm) to $+11°$ (1.5 μm) from sin $\alpha$+sin $\beta$=Ng1$\lambda$. Accordingly, the interference light beam L4 of $\Delta\Lambda=200$ nm based on the low coherence light L which is 1.3 μm in the central wavelength ($\lambda 0=1.3$ μm) and 150 nm in $\Delta\lambda$ ($\Delta\lambda=150$ nm) can be detected in the light detecting means 44.

Whereas, when the diffraction grating 142b is employed in the measurement initiating position adjusting mode as shown in FIG. 6B, the radiation angle $\beta$ when the interference light beam L4 impinges upon the spectral means 43 form the optical fiber FB4 at angle of incidence $\alpha=80°$ is 32° (1.26 μm) to 46° (1.42 μm) from sin $\alpha$+sin $\beta$=Ng2$\lambda$. Accordingly, only a light beam narrower than the measuring wavelength band in the image obtaining mode out of the interference light beam L4 based on the low coherence light L which is 1.3 μm in the central wavelength ($\lambda 0=1.3$ μm) and 150 nm in $\Delta\lambda$ ($\Delta\lambda=150$ nm) is detected in the light detecting means 44. The wavelength band ΔΛ is substantially a half and the measurable range is substantially doubled at this time. Accordingly, the object S can be easily imaged in a tomographic image, and the optical path length can be adjusted simply at high speed. Though, in the description above, a pair of diffraction gratings 142a and 142b are employed, by way of example, more than two diffraction gratings may be used.

Figure 7:
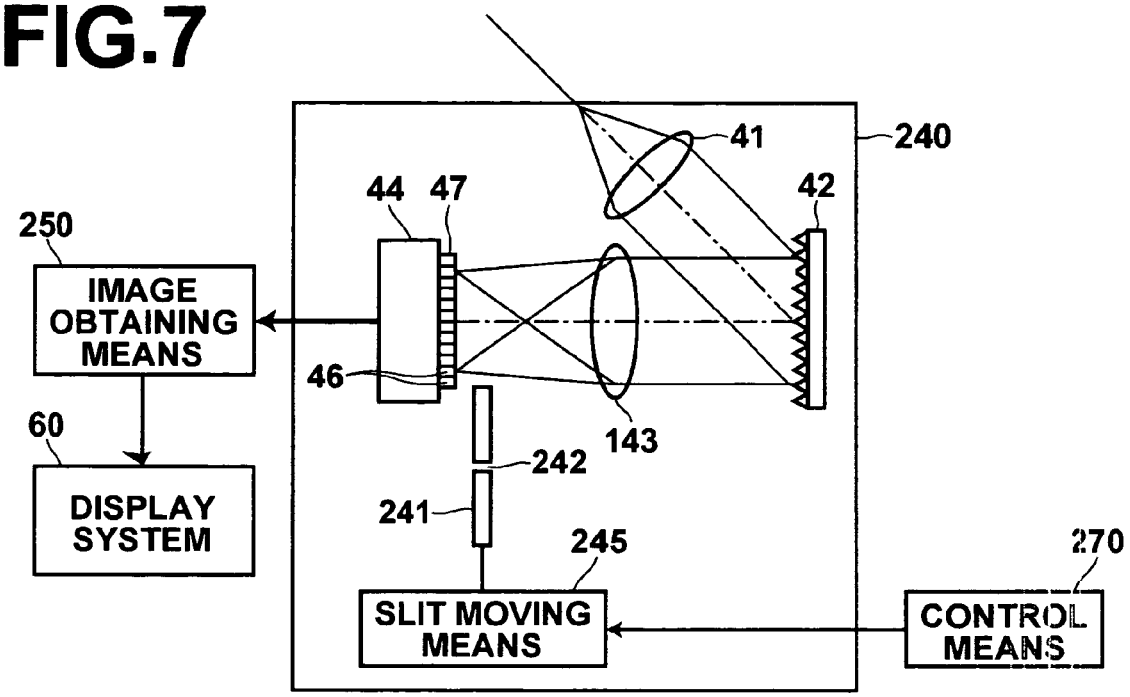
FIG. 7 is a schematic diagram showing a third example of the interference light detected in the interference light detecting means in the optical tomography system of the present invention.
Figure 8:
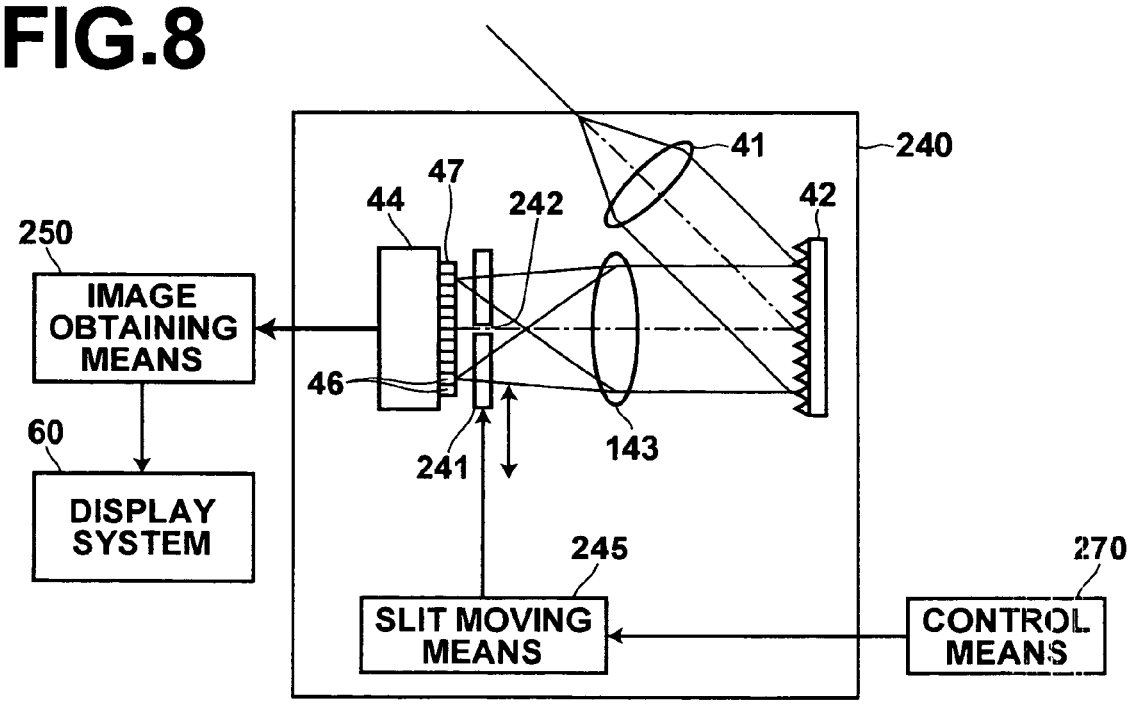
FIG. 8 is a schematic diagrams showing a third example of the interference light detected in the interference light detecting means in the optical tomography system of the present invention.
Figure 9:
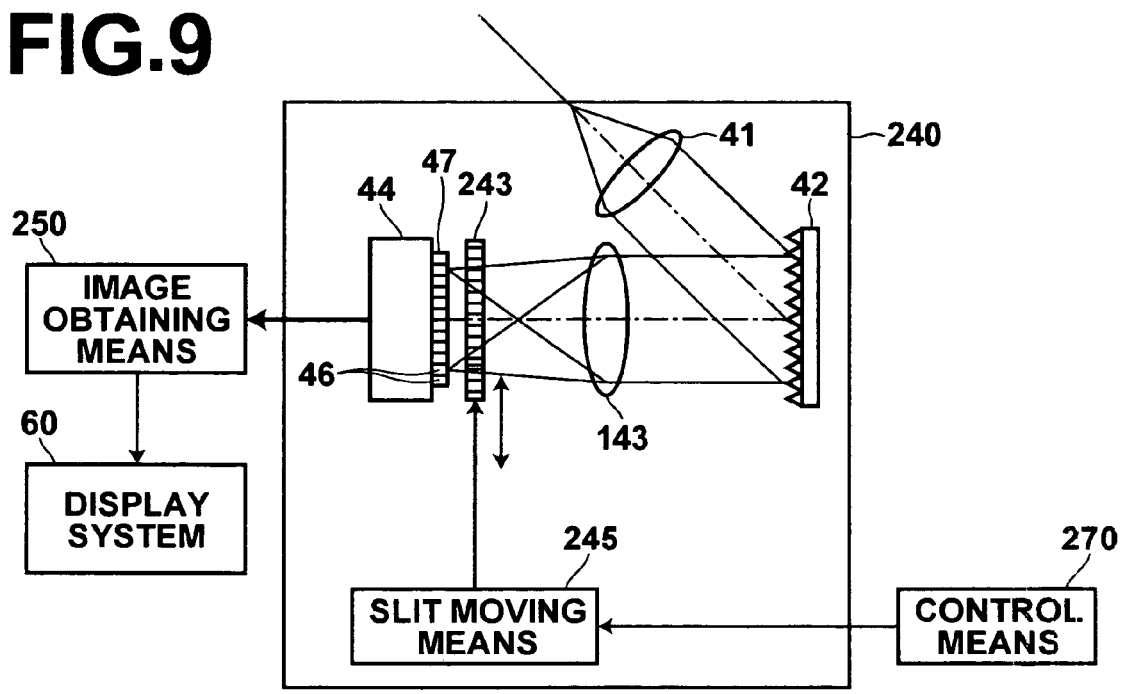
FIG. 9 is a schematic diagram showing a modification of the third example of the interference light detected in the interference light detecting means in the optical tomography system of the present invention.
Figure 10:
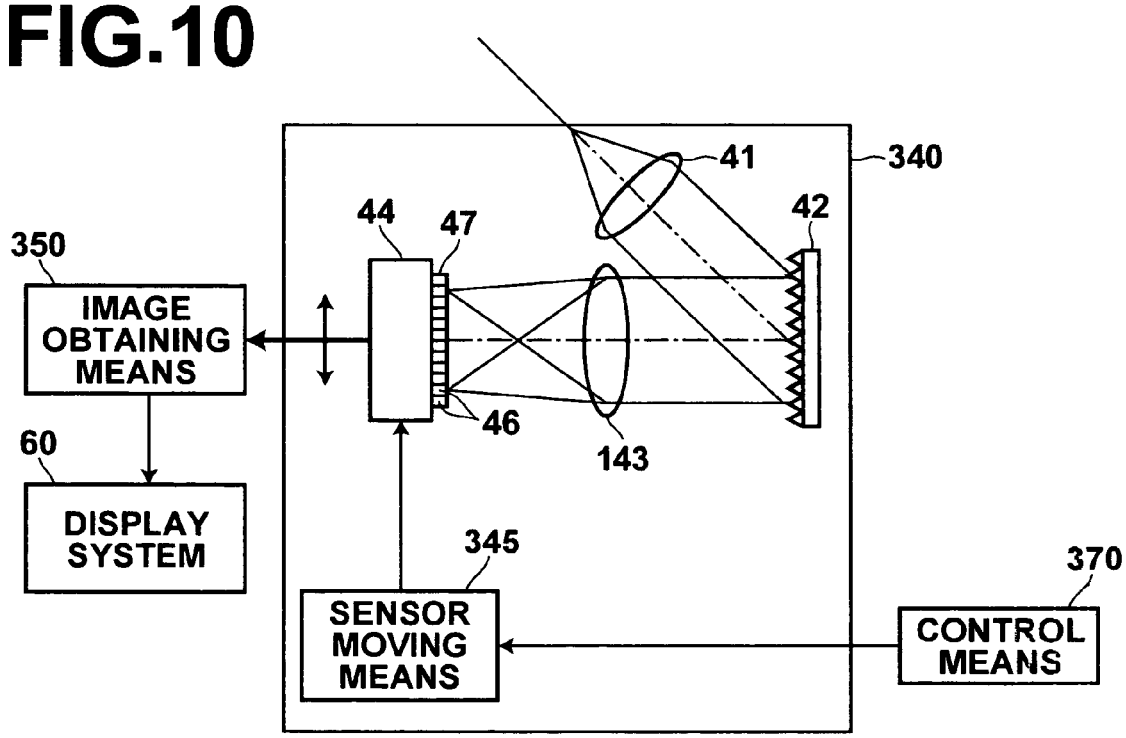
FIG. 10 is a schematic diagram showing a fourth example of the interference light detected in the interference light detecting means in the optical tomography system of the present invention.

Otherwise, when each of the photo-sensors 46 of the optical sensor 47 of the light detecting means 44 detects the different wavelengths of the interference light L4 at different times, the number N of the optical sensor 47 apparently increases, which improves the wavelength resolution of the interference light detecting means, whereby the obtainable range Δllim is increased. (See formula (4).) Specific ways include a way in which a slit element is moved as shown in FIGS. 7, 8 and 9, a way in which the optical sensor 47 is moved as shown in FIG. 10 and a way in which the optical path of the interference light is shifted as shown in FIGS. 11 to 14. The elements of the interference light detecting means 240, 340, 440 and 540 shown FIGS. 7 to 14 analogous to those in the interference light detecting means 40 and 140 shown in FIGS. 5 and 6 are given the same reference numerals and will not be described in detail, here. In this case, the light detecting means 44 detects, a plurality of times, at different times in order to obtain one optical tomographic image. The image obtaining means 250, 350, 450 or 550 obtains the information on reflection in positions in the direction of depth by carrying out frequency-analysis on the reflected light beams L4 detected a plurality of times by the interference light detecting means 40 and obtains a tomographic image of the object S by the use of the intensities of the reflected light L3 in each of the positions in the direction of depth.

The interference light detecting means 240 shown in FIG. 7 comprises a slit element 241 which is to be inserted between the spectral means and the light detecting means 44 and transmits only a part of the wavelength band of the interference light L4 toward the light detecting means 44, and a slit moving means 245 which inserts the slit element 241 between the spectral means and the light detecting means 44. Slit 242 which is smaller in width than the light receiving face of one photo-sensor 46 of the optical sensor 47 is provided in the slit element 241. The control means 70 controls the slit moving means 245 to insert the slit element 241 between the light detecting means 44 and the spectral means 42 only in the measurement initiating position adjusting mode.

Specifically, the control means 70 does not insert the slit element 241 in the image obtaining mode as shown in FIG. 7. On the other hand, the control means 70 inserts the slit element 241 in the measurement initiating position adjusting mode as shown in FIG. 8. Then only the interference light L4 of particular wavelengths passing through the slit 242 is detected by the optical sensor in each sampling. Further, one photo-sensor 46 (one pixel) detects the interference light L4 at a different wavelength by moving the slit 241 at spaces narrower than the spaces between photo-sensors in the direction in which the photo-sensors 46 are arranged (in the direction in which the interference light L4 are spectrally divided) by the slit moving means 245. That is, the number N of photo-sensors in the optical sensor 47 can be apparently increased to improve the wavelength resolution. With this arrangement, the image obtainable range Δllim can be widened so that the object S can be easily imaged in a tomographic image, and the optical path length can be adjusted simply at high speed.

The slit element may be provided with a plurality of silts. For example, a slit element 243 having a plurality of slits the same as the photo-sensors in number may be employed. By increasing the number of slits, the number by which the slit element is to be moved is reduced and increase in the measuring time can be suppressed.

In the interference light detecting means 340 shown in FIG. 10, a sensor moving means 345 which moves the light detecting means 44 in the direction in which the photo-sensors 46 are arranged is provided. The control means 70 controls the sensor moving means 345 in the measurement initiating position adjusting mode to move the light detecting means 44 by an amount smaller than the width of the light receiving face of the photo-sensor 46 (one pixel). With this arrangement, each of the photo-sensors 46 detects the interference light beam L4 at different wavelength at different times before and after the movement and the number N of photo-sensors in the optical sensor 47 can be apparently increased to improve the wavelength resolution. As a result, the image obtainable range Δllim can be widened so that the object S can be easily imaged in a tomographic image, and the optical path length can be adjusted simply at high speed. The movement of the light detecting means 44 may only have not to be equivalent to the space between photo-sensors and may be, for instance, 1.5 pieces of the photo-sensors.

Figure 11:
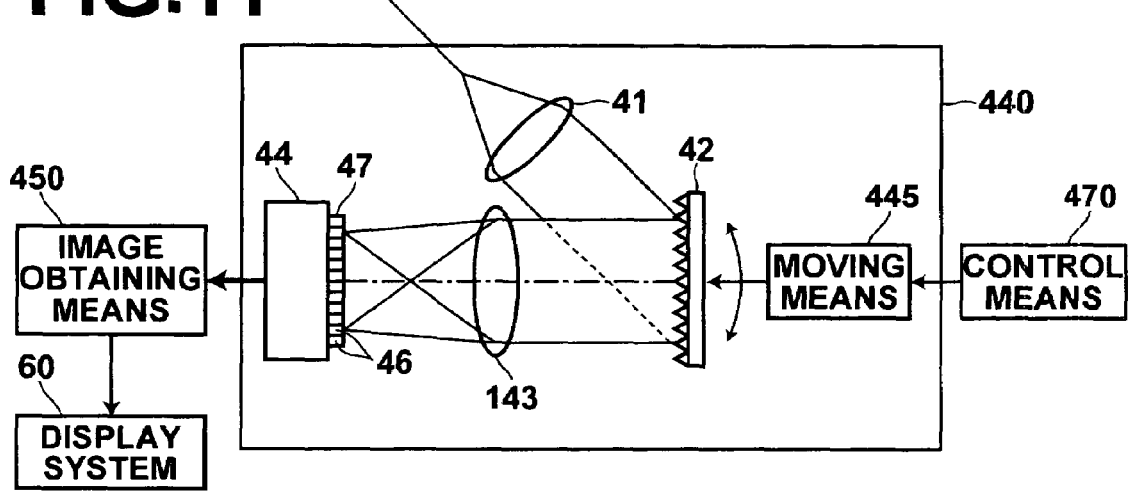
FIG. 11 is a schematic diagram showing a fifth example of the interference light detected in the interference light detecting means in the optical tomography system of the present invention.

In the interference light detecting means 440 shown in FIG. 11, a moving means 445 for moving the spectral means 42 is provided and the moving means 445 is controlled by the control means 470. The control means 470 controls the moving means 445 in the measurement initiating position adjusting mode to move, for instance, rotate the spectral means 42 so that the interference light beam L4 at different wavelength is projected onto each of the optical-sensors of the light detecting means 44 at different times. With this arrangement, the number N of photo-sensors in the optical sensor 47 can be apparently increased to improve the wavelength resolution. As a result, the image obtainable range Δllim can be widened so that the object S can be easily imaged in a tomographic image, and the optical path length can be adjusted simply at high speed. The direction of movement of the spectral means 42 may be any direction so long as the wavelength band of the interference light beam L4 entering the photo-sensors 46 changes and the movement is not limited to rotation. For example, the spectral means 42 may be translated in a direction along the optical axis of the interference light beam L4 entering the spectral means 42.

Figure 12:
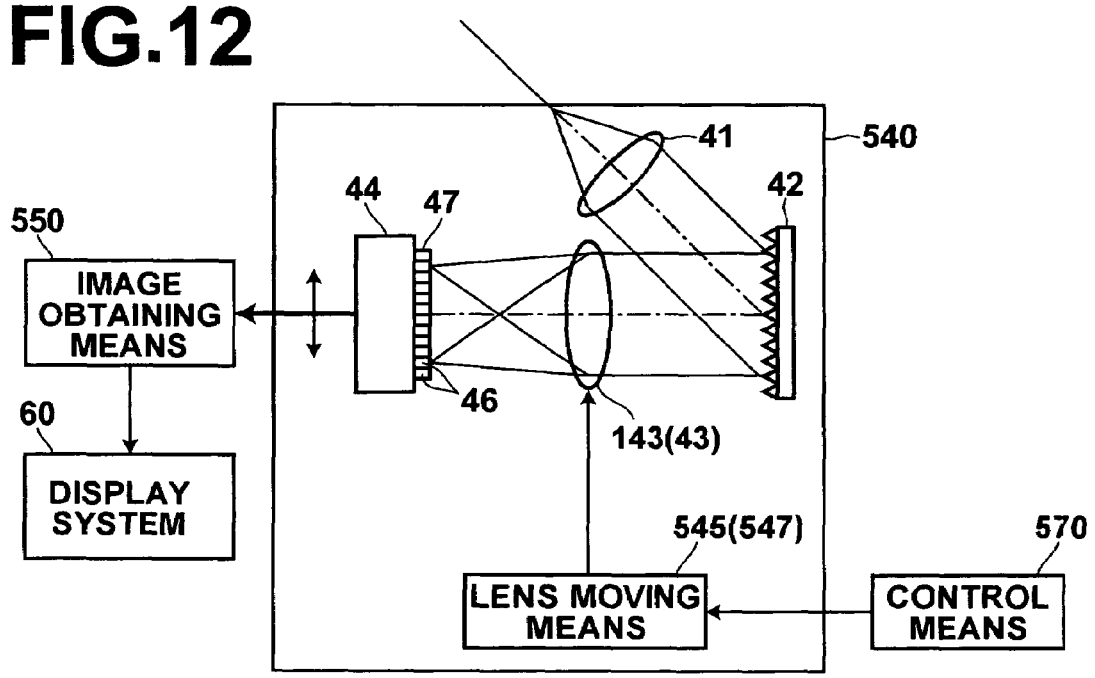
FIG. 12 is a schematic diagram showing a sixth example of the interference light detected in the interference light detecting means in the optical tomography system of the present invention.

In the interference light detecting means 540 shown in FIG. 12, a moving means 545 for moving the lens 143 is provided and the moving means 545 is controlled by the control means 570. The control means 570 controls the moving means 545 in the measurement initiating position adjusting mode to move the lens 143 toward the photo-sensors 46 so that the interference light beam L4 at different wavelength is projected onto each of the optical-sensors of the light detecting means 44 at different times. With this arrangement, the number N of photo-sensors in the optical sensor 47 can be apparently increased to improve the wavelength resolution. As a result, the image obtainable range Δllim can be widened so that the object S can be easily imaged in a tomographic image, and the optical path length can be adjusted simply at high speed. The direction of movement of the spectral means 42 may be any direction so long as the wavelength band of the interference light beam L4 entering the photo-sensors 46 changes and the movement may be movement along the optical axis of the interference light beam L4 or rotation. Further, instead of the lens 143, a zoom lens 43 shown in FIG. 1 may be employed. In this case, instead of the lens moving means 545, a lens moving/drive means 547 having a function of the lens moving means 545 in addition to the function of the zooming means 45 shown in FIG. 1 only has to be employed.

When a large measuring resolution is not necessary as when the measurement initiation position is to be adjusted, magnification of the zoom lens is increased so that a part wavelength band ΔΛb of the whole wavelength band ΔΛa of the interference light L4 is caused to enter the optical sensor 47. With this arrangement, the wavelength band to be detected by each of the photo-sensors 46 of the optical sensor 47 is narrowed and the wavelength resolution of the light detecting means 44 is improved. In this case, though the measuring resolution is reduced, an optical tomographic image which is large in measurable range (measuring depth) can be obtained without increasing the measuring time. As a result, the image obtainable range Δllim can be widened.

When a large measuring resolution is necessary as when a layer arrangement of the stomach wall is to be observed, the position of the zoom lens 43 is moved so that the interference light beam L4 at different wavelength is detected by each photo-sensor 46 of the optical-sensor 47. With this arrangement, the apparent wavelength resolution in the light detecting means 44 is improved. In this case, though the measuring time is increased, an optical tomographic image which is large in measurable range (measuring depth) can be obtained without deteriorating the measuring resolution.

Figure 13:
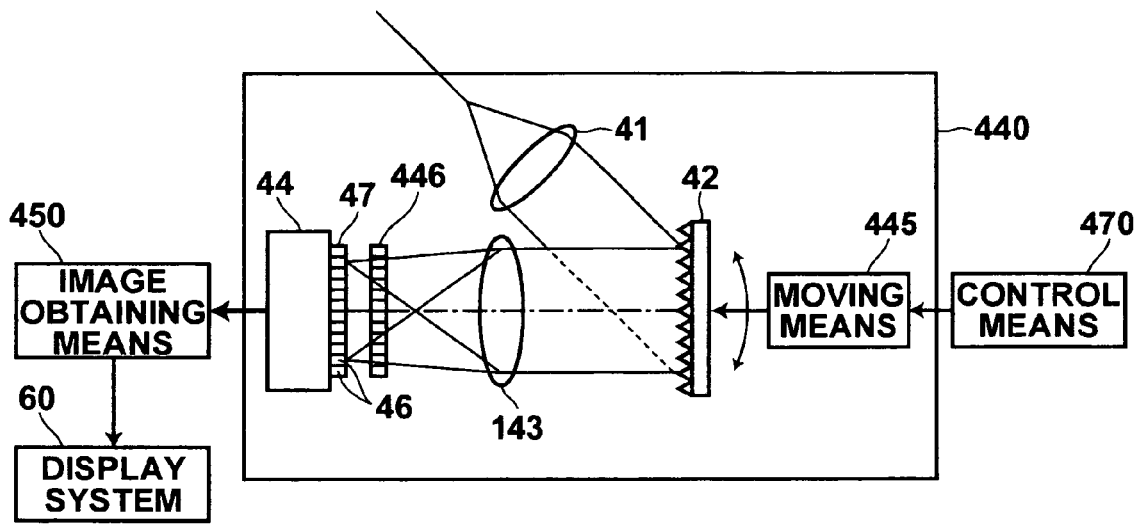
FIG. 13 is a schematic diagram showing a modification of the fifth example of the interference light detected in the interference light detecting means in the optical tomography system of the present invention.
Figure 14:
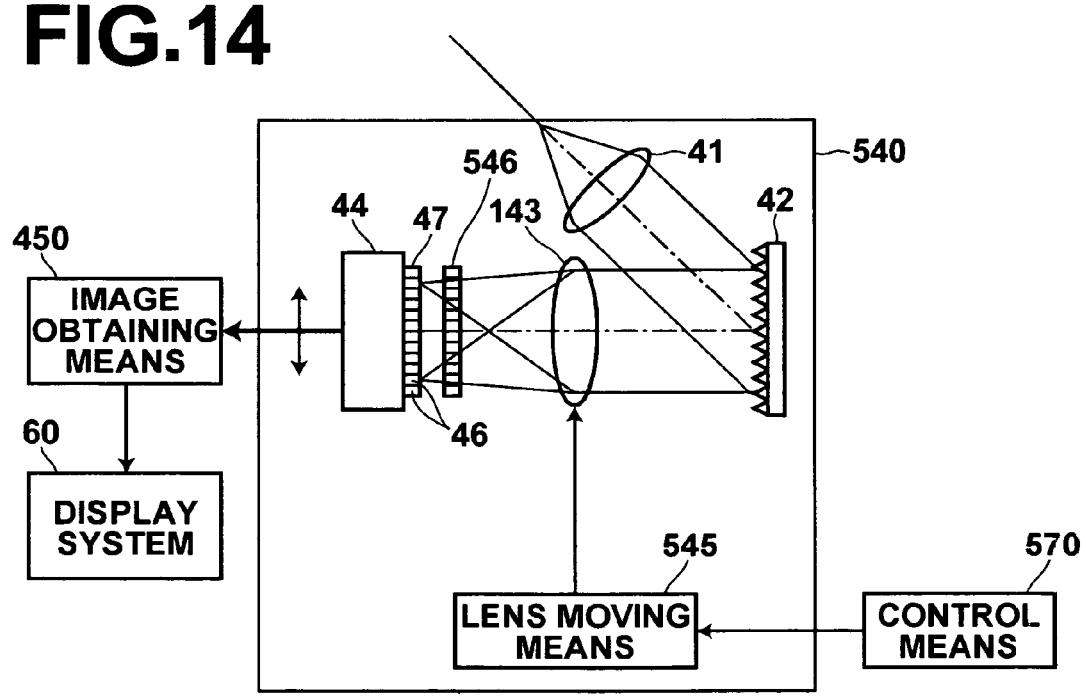
FIG. 14 is a schematic diagram showing a modification of the sixth example of the interference light detected in the interference light detecting means in the optical tomography system of the present invention.

Further, as shown in FIG. 13, in the interference light detecting means shown in FIG. 11, a slit element 446 may be inserted between the light detecting means 44 and the spectral means 42 in the measurement initiating position adjusting mode. In this case, the wavelength of the light passing through the slit element changes when the spectral means 42 is moved, that is, the spectral means 42 is rotated or translated along the optical axis of the interference light beam L4 entering the spectral means 42, with the slit element 446 held stationary. That is, one photo-sensor (one pixel) can detect the interference light beam L4 at different wavelengths at different times. Further, as shown in FIG. 14, in the interference light detecting means shown in FIG. 12, a slit element 546 may be provided.

Also in the case where the optical sensor thus detects the interference light L4 at a different wavelengths at a different times to increase the wavelength resolution, it is possible to improve the wavelength resolution of the interference light detecting means and to widen the measurable range so that the object can be easily found in the measurement initiating position adjusting mode. Accordingly, a tomographic image of the object can be easily obtained in the measurement initiating position adjusting mode, and the measurement initiating position can be efficiently adjusted. Though, in FIGS. 7 to 13, it takes a longer time in the measurement initiating position adjusting mode than in the image obtaining mode, obtaining a tomographic image at high speed is not so required in the measurement initiating position adjusting mode as in the image obtaining mode.

The present invention is not limited to the above embodiments. For example, though, in FIG. 3, a part of the interference light beam L4 is caused to impinge upon the light detecting means 44 by the use of a zooming function of the zoom lens 43, a part of the interference light beam L4 may be caused to impinge upon the light detecting means 44 without use of a zooming function of the zoom lens 43 by moving the light detecting means 44 in the direction of the optical axis of the interference light beam L4 or by changing the distance between the light outlet ends of the lens 41 and the optical fiber FB4. Otherwise, the light detecting means 44 may be replaced.

Further, though changing the diffraction grating for a diffraction grating different in spaces Ng between the gratings is described, by way of example, in FIG. 5, when the interference light detecting means has a separately provided spectral means which detects the light beam of each wavelength band of the interference light beam L4 by a so-called grating scan system, the interference light beam L4 may be caused to impinge upon the separately provided spectral means.

Figure 15:
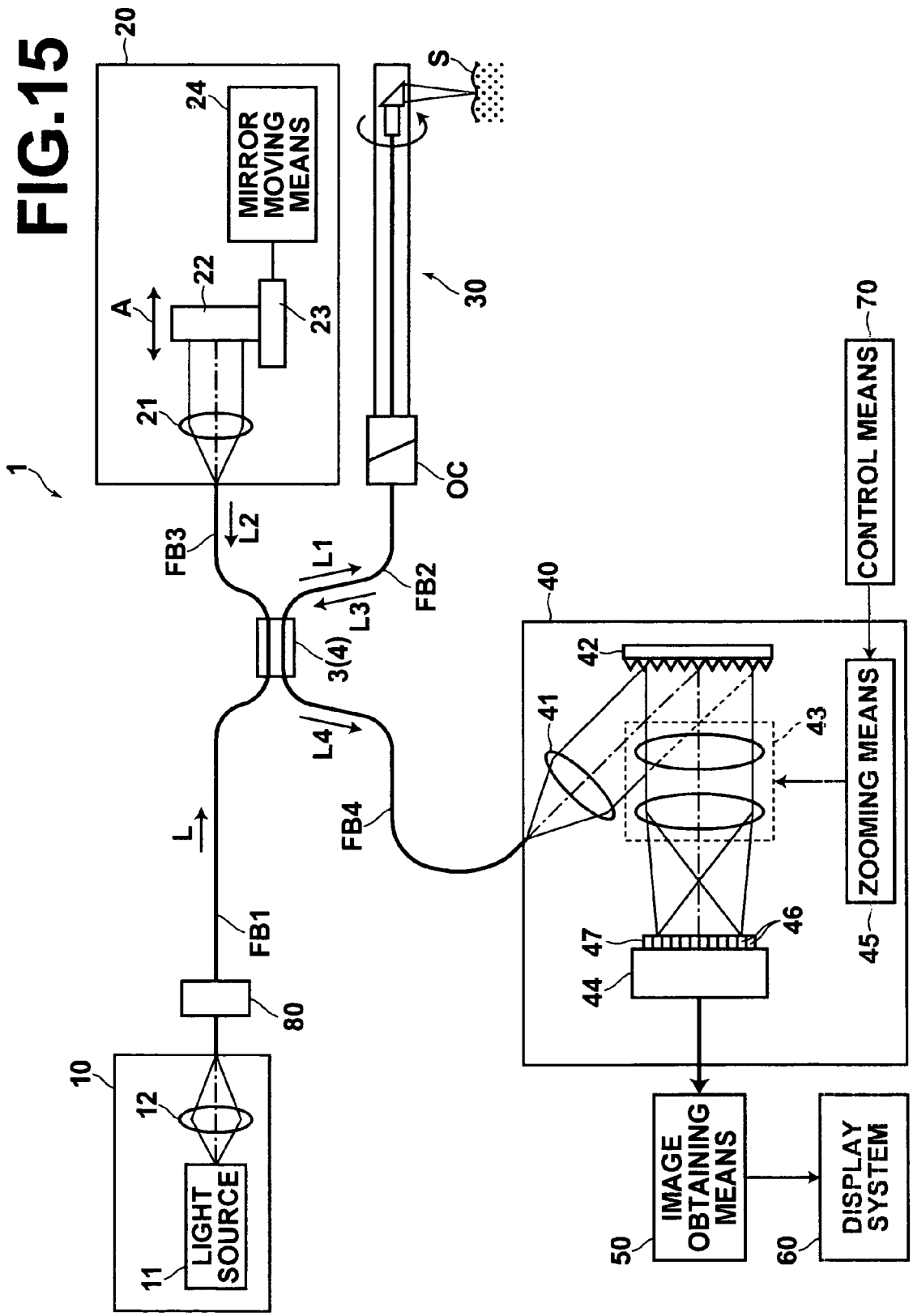
FIG. 15 is a schematic diagram showing a modification of the sixth example of the interference light detected in the interference light detecting means in the optical tomography system of the present invention.

In each of the above embodiments, a Gaussian distribution filter 80 which is a filter for wavelength forming may be inserted into an optical path of the low coherence light beam L as shown in FIG. 15. In this case, even if the spectrum of the low coherence light L emitted from the light source 11 includes ripples as shown in FIG. 15, the spectrum is corrected by the Gaussian distribution filter 80 to a form exhibiting Gaussian distribution and deterioration of the measuring accuracy can be suppressed.

Figure 16:
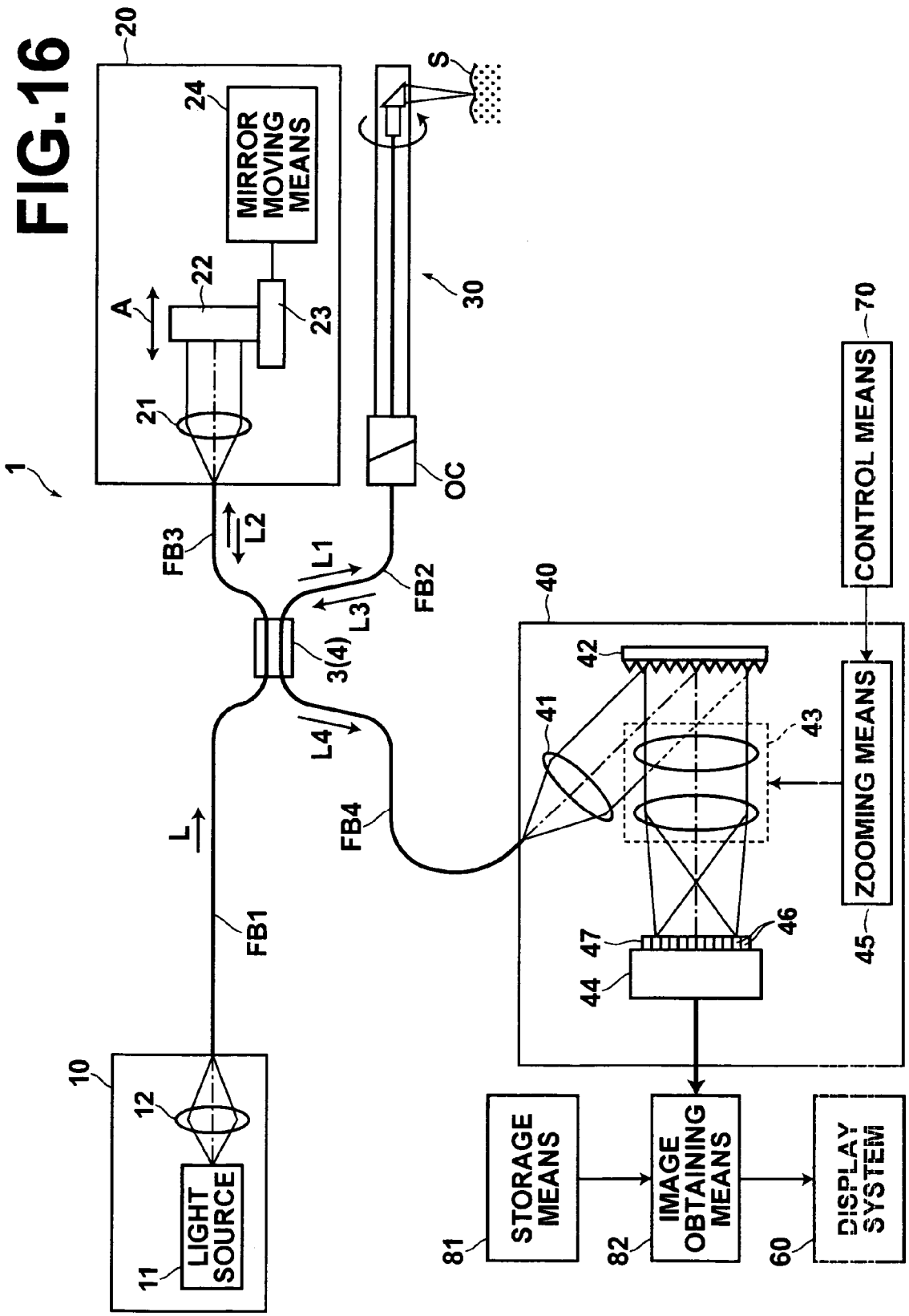
FIG. 16 is a schematic diagram showing a modification of the sixth example of the interference light detected in the interference light detecting means in the optical tomography system of the present invention.

Further, when the spectrum of the low coherence light L emitted from the light source 11 includes ripples, the optical tomography system of each embodiment may comprise a memory means 81 for storing the spectral components of the measured measuring light L1, and an image obtaining means 82 which generates a compensating signal by removing the spectral components of the measuring light L1 stored in the memory means 81 from an interference signal obtained by detecting the interference light L4 and obtains information on a cross-section of the object on the basis of the compensating signal as shown in FIG. 16.

Ripples superimposed on the spectrum of the light source 11 appears as a side lobe in a signal after Fourier-transform. Since the side lobe is apparently the same as the component which shows existence of a reflecting interface in a position of depth, the side lobe makes noise to the reflection information and deteriorates the image quality of the tomographic image.

When the signal component representing the spectrum of the light source is represented by So(k) and the reflected component is represented by R(k), Si(k) can be expressed by the following formula.

$$Si(k)=So(k)\{1+R(k)\} \quad (5)$$

When the spectrum of the light source is known as advance information, the compensating signal R(k) where only the reflected component is extracted with the spectral components of the measuring light removed can be obtained by carrying out calculation on the basis of the following formula (6).

$$R(k)=\{Si(k)/So(k)\}-1 \quad (6)$$

Since when carrying out Gaussian-transform on the compensating signal, the signal after the Gaussian-transform becomes similar to the interference signal in the case where a measuring light beam which is of an ideal Gaussian-form in spectral form is employed, appearance of the above noise can be prevented by carrying out Fourier-transform on it.

On the basis of the things described above, in the system shown in FIG. 16, the light L as it is led to the interference light detecting means 40 before a tomographic image is obtained, and the spectrum of the light L is measured by the light detecting means 44. The signal So representing this spectrum is stored in the memory means 81 as compensating data. Then, when obtaining a tomographic image, the image obtaining means 82 carries out calculation of formula (2) from the signal Si(k) obtained and the spectral signal So(k) read out from the memory means 81, and carries out Gaussian-transform on the compensating signal R(k) obtained. Further, the image obtaining means 82 carries out Fourier-transform on the signal after transform. By this, even if the spectral shape of the measuring light L1 deviates from the Gaussian-form or the spectral shape and the intensity of the measuring light L1 fluctuate, appearance of the above noise can be prevented and an accurate tomographic image can be stably obtained.

What is claimed is:

1. An optical tomography system for obtaining a tomographic image of an object to be measured comprising:
   a light source unit which emits low coherence light,
   a light dividing means which divides the low coherence light emitted from the light source unit into measuring light and reference light,
   a combining means which combines a reflected light from the object when the measuring light is projected onto the object and the reference light,
   an interference light detecting means which detects interference light of the reflected light and the reference light which have been combined by the combining means, and
   a tomographic image information obtaining means which obtains a tomographic image information of the object by carrying out frequency-analysis on the interference light detected by the interference light detecting means, and
   the interference light detecting means being able to be switched between a first detecting mode in which the interference light detecting means detects the interference light at a first wavelength resolution and a second detecting mode in which the interference light detecting means detects the interference light at a second wavelength resolution higher than the first wavelength resolution, wherein
   the interference light detecting means comprises a spectral means which spectrally divides the interference light, an optical sensor which detects the interference light divided by the spectral means and comprises a plurality of arranged photo-sensors, and a wavelength bandwidth switching means which switches the wavelength bandwidth of the interference light entering the optical sensor,
   the wavelength bandwidth switching means comprises a spectral angular width changing means which switches the spectral angular width of the interference light, and
   the wavelength bandwidth switching means comprises a plurality of diffraction gratings different in grating spaces and a diffraction grating selecting means which selectively disposes in a spectral dividing position where the interference light can be spectrally divided by one of the diffraction gratings.

2. An optical tomography system as defined in claim 1, in which the diffraction grating selecting means selects the diffraction grating such that the grating space of the diffraction grating disposed in the second detecting mode is narrower than the grating space of the diffractions grating disposed in the first detecting mode.

3. An optical tomography system as defined in claim 1, wherein the diffraction grating selecting means selectively disposes one of the plurality of diffraction gratings to the spectral dividing position, wherein the plurality of diffraction gratings are interchangeably switched in and out of the spectral dividing position with one another according to a selection of the diffraction grating selecting means.

4. An optical tomography system as defined in claim 3, wherein the entire interference light is spectrally divided by one of the plurality of diffraction gratings at a single position corresponding to the spectral dividing position, the entire interference light being selectively divided among the plurality of diffraction gratings.

5. An optical tomography system as defined in claim 4, where the entire interference light is spectrally divided at the spectral dividing position by any one of the plurality of diffraction gratings.

6. An optical tomography system for obtaining a tomographic image of an object to be measured comprising
   a light source unit which emits low coherence light,
   a light dividing means which divides the low coherence light emitted from the light source unit into measuring light and reference light,
   a combining means which combines a reflected light from the object when the measuring light is projected onto the object and the reference light,
   an interference light detecting means which detects interference light of the reflected light and the reference light which have been combined by the combining means, and being able to be switched between a first detecting mode in which the interference light detecting means detects the interference light at a first wavelength resolution and a second detecting mode in which the interference light detecting means detects the interference light at a second wavelength resolution higher than the first wavelength resolution,
   a tomographic image information obtaining means which obtains a tomographic image information of the object by carrying out frequency-analysis on the interference light detected by the interference light detecting means, and wherein
   the interference light detecting means comprises a spectral means which spectrally divides the interference light into a spectrum of light, an optical sensor comprises a plurality of photo detectors and detects parts of the spectrum of light divided by the spectral means, and a spectrum shifting means which shifts said parts of the spectrum of light incident on said plurality of photo detectors at different times in the second detecting mode,
   the tomographic image information obtaining means obtains a tomographic image information of the object based on output detected by said plurality of photo detectors at different times in the second mode,
   the spectrum shifting means comprises an optical path shift means which spatially shifts the optical path of the interference light so that the parts of the spectrum of light incident on said plurality of photo detectors are shifted at different times, and
   the optical path shift means comprises:
      a collective lens which is disposed between the optical sensor and the spectral means and which collects the interference light which has been spectrally divided by the spectral means on the optical sensor; and
      a collective lens moving means which moves the collective lens so that the parts of the spectrum of light incident on said plurality of photo detectors are shifted at different times.

7. An optical tomography system as defined in claim 6 in which the spectrum shifting means comprises a slit element having a slit narrower than a light receiving face of each of the plurality of photo detectors in a width in a direction in which the plurality of photo detectors are arranged and a slit moving means which moves the slit element in the direction in which the plurality of photo detectors are arranged.

8. An optical tomography system as defined in claim 6 in which the spectrum shifting means comprises an optical sensor moving means which moves the optical sensor so that the parts of the spectrum of light incident on said plurality of photo detectors are shifted at different times.

9. An optical tomography system as defined in claim 6 in which the first detecting mode is an image obtaining mode where a tomographic image of the object is obtained while the second detecting mode is a measurement initiating position adjusting mode where a position of obtaining a tomographic image signal is adjusted in the direction of depth of the object, and the optical tomography system further comprises a control means which switches between the image obtaining mode and the measurement initiating position adjusting mode.

10. An optical tomography system as defined in claim 6 further comprising an optical path length adjusting means which adjusts the optical path length of the measuring light or the reference light.

11. An optical tomography system as defined in claim 6 in which a wavelength filter may be inserted in the optical path of the low coherence light or the measuring light.

12. An optical tomography system as defined in claim 6 in which the optical tomography system comprises a means for measuring the spectral components of the measuring light and a memory means for storing the measured spectral components, and the tomographic image information obtaining means obtains the tomographic image information of the object on the basis of a compensating signal by generating the compensating signal by removing the spectral components of the measuring light stored in the memory means from an interference signal detected by the interference light.

* * * * *